United States Patent [19]

Winston et al.

[11] Patent Number: 5,366,473
[45] Date of Patent: * Nov. 22, 1994

[54] METHOD AND APPARATUS FOR APPLYING VASCULAR GRAFTS

[75] Inventors: Thomas R. Winston, Leawood; John M. Neet, Shawnee, both of Kans.

[73] Assignee: Ultrasonic Sensing and Monitoring Systems, Inc., Leawood, Kans.

[*] Notice: The portion of the term of this patent subsequent to Apr. 26, 2010 has been disclaimed.

[21] Appl. No.: 931,675

[22] Filed: Aug. 18, 1992

[51] Int. Cl.⁵ ............................................... A61F 2/06
[52] U.S. Cl. ................................... 606/198; 623/12
[58] Field of Search ............... 606/191, 194, 108, 198; 623/1, 12; 128/20

[56] References Cited

U.S. PATENT DOCUMENTS

| | | | |
|---|---|---|---|
| 4,140,126 | 2/1979 | Choudhury | 606/194 |
| 4,733,665 | 3/1988 | Palmaz . | |
| 4,763,653 | 8/1988 | Rockey | 606/194 |
| 4,969,458 | 11/1990 | Wiktor | 606/194 |
| 4,994,071 | 2/1991 | MacGregor | 606/194 |
| 5,007,926 | 4/1991 | Derbyshire | 623/1 |
| 5,019,085 | 5/1991 | Hillstead | 606/108 |
| 5,026,377 | 6/1991 | Burton et al. | 606/108 |
| 5,041,126 | 8/1991 | Gianturco | 606/195 |
| 5,078,720 | 1/1992 | Burton et al. | 606/108 |
| 5,078,726 | 1/1992 | Kreamer | 606/194 |
| 5,100,429 | 3/1992 | Sinofsky et al. | 606/195 |
| 5,108,417 | 4/1992 | Sawyer | 606/198 |
| 5,147,370 | 9/1992 | McNamara et al. | 606/108 |
| 5,151,105 | 9/1992 | Kwan-Gett | 623/1 |

FOREIGN PATENT DOCUMENTS

| | | | |
|---|---|---|---|
| 694197 | 10/1979 | U.S.S.R. | 606/194 |
| 82/03333 | 10/1982 | WIPO | 606/194 |
| 91/15254 | 10/1991 | WIPO . | |
| 91/17789 | 11/1991 | WIPO . | |

Primary Examiner—Tamara L. Graysay
Attorney, Agent, or Firm—Hovey, Williams, Timmons & Collins

[57] ABSTRACT

A vascular graft is held in a collapsed state on a pair of stents which take the form of flexible sheets wound around a spool. A sheath is fitted closely around the graft to hold it in its collapsed state and to retain the stents in rolls tightly wound on the spool. After the spool has been inserted into a damaged vessel and advanced to the area of vascular damage, the sheath is withdrawn. The stents then unwind and expand to press the ends of the graft against healthy parts of the vessel on opposite sides of the damaged area. An alternative embodiment of the invention includes a Y-shaped graft for application to a branched part of a vessel. In place of a sheath, control cords with slip knots are used to retain the stents in their contracted conditions while the graft is being positioned in the vessel. The control cords can be pulled to release the slip knots and permit the stents to expand in a manner to secure two branch portions of the graft in the vessel branches and a trunk portion of the graft in the main trunk of the vessel.

11 Claims, 2 Drawing Sheets

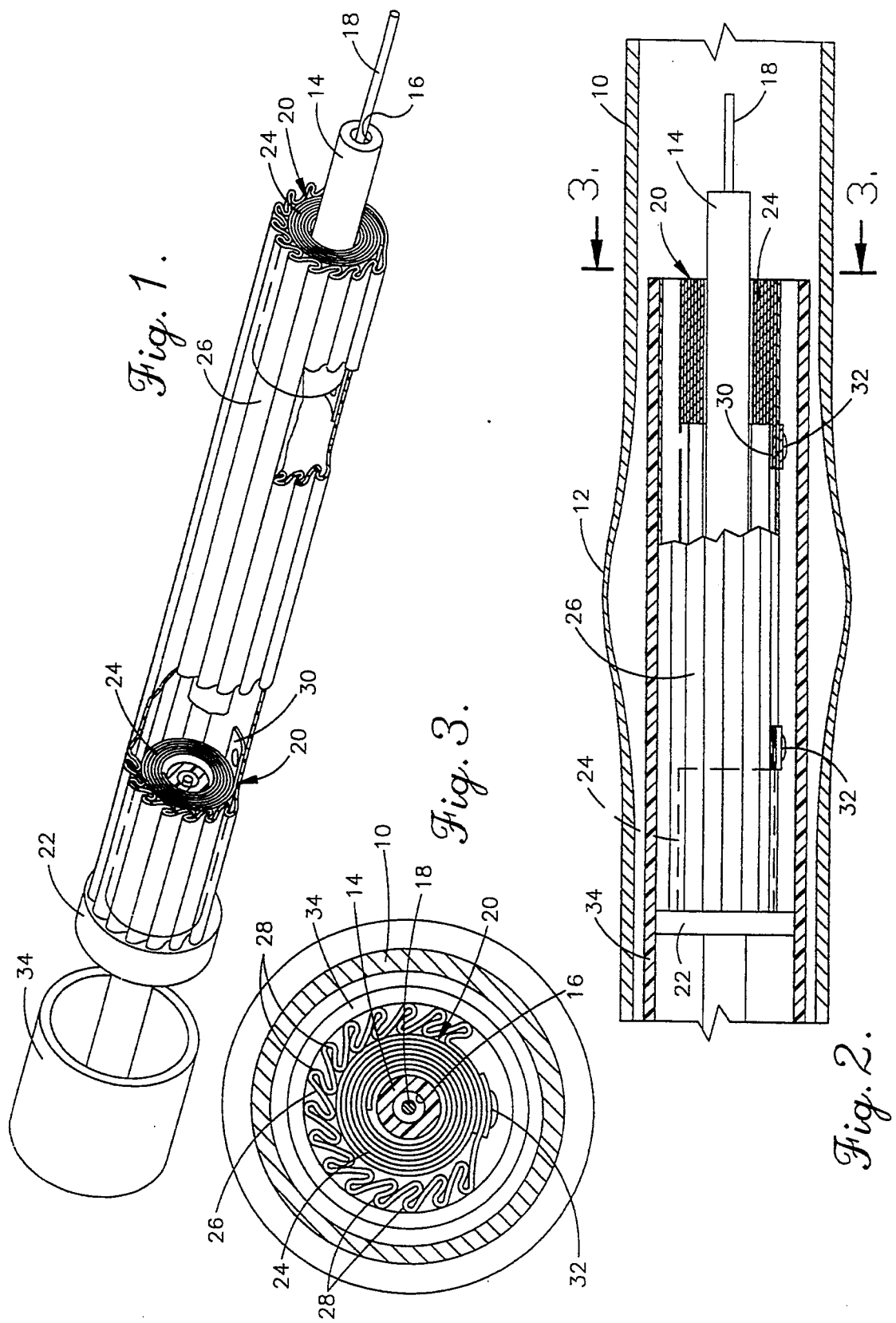

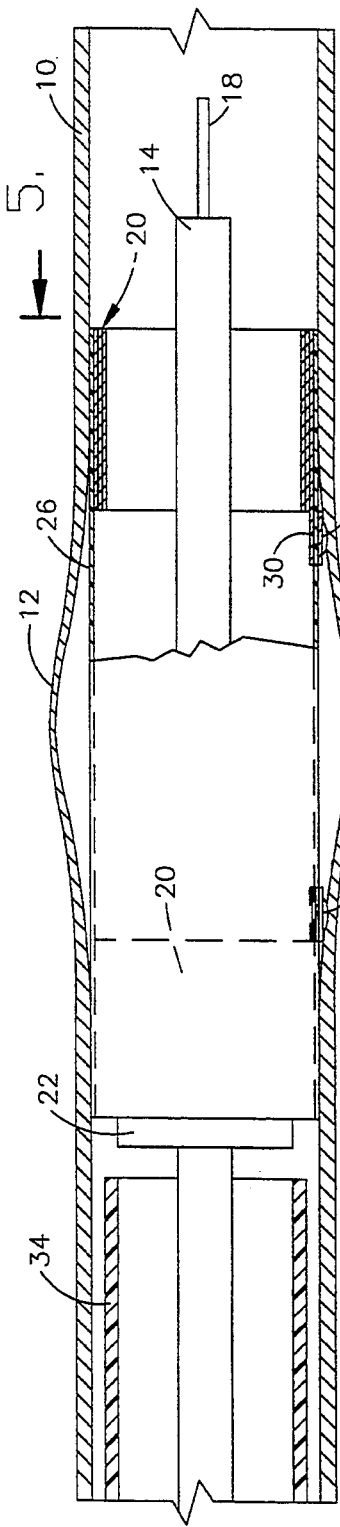
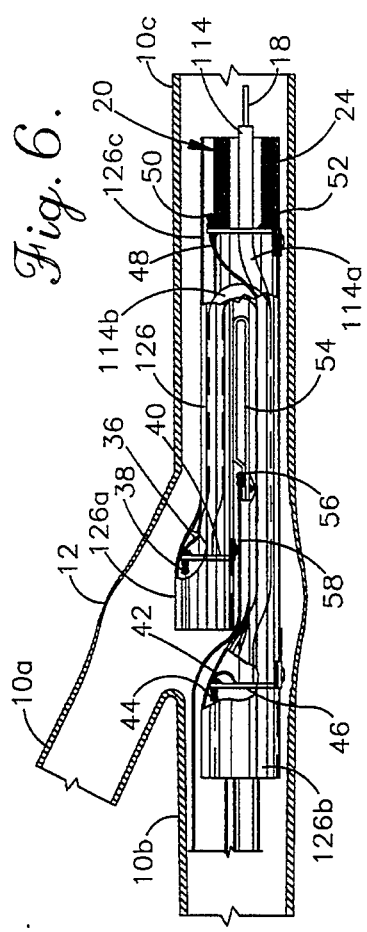
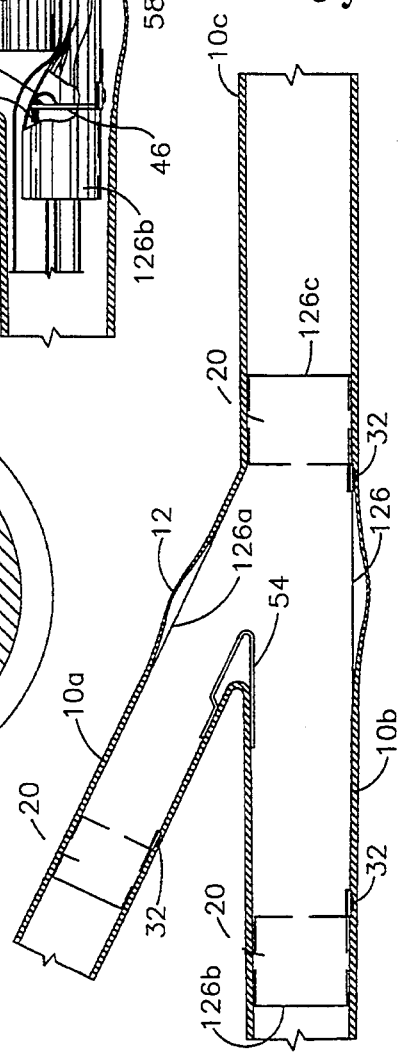

5,366,473

METHOD AND APPARATUS FOR APPLYING VASCULAR GRAFTS

FIELD OF THE INVENTION

This invention relates in general to the implantation of vascular grafts and more particularly to a method and apparatus for applying and securing a graft in place in a damaged vessel.

BACKGROUND OF THE INVENTION

The walls of arteries and blood vessels can become damaged by disease or a number of other causes, including medical treatments such as angioplasty. One technique that has been used to repair damaged vessels and arteries is invasive surgery. Typically, incisions are made in the area of the damaged vessel, and it is resected and replaced either by a synthetic graft or by a healthy vessel that is removed from the patient at a different portion of his or her body. The graft is typically sutured in place. While this technique is often effective, it is characterized by the trauma and other problems that are associated with major surgery. In the case of patients who are in poor health or in a weakened condition, invasive surgery is not always possible.

As disclosed in U.S. Pat. No. 5,078,726 to Kreamer, prior inventors have proposed holding vascular grafts in place through the use of expansible stents. The principal problems with the stents proposed in the Kreamer patent is that they are naturally contracted and must be positively expanded in order to be able to hold the graft in place. Consequently, a balloon catheter or other device must be inserted into the vessel to the area of the stents and expanded in order to expand the stents. The need to make use of a balloon catheter increases the difficulty involved in properly applying the graft. In addition, it increases the time that is needed for the procedure and requires highly skilled and experienced medical personnel. The stents are not always properly applied even then, and their ability to hold the graft in place suffers accordingly.

Another drawback with the Kreamer device is that the stents have a fixed diameter in the expanded condition. Consequently, it is necessary for the stent to closely conform with the diameter of the blood vessel in order to properly perform its intended function. If the stent is too large, it can unduly expand and the healthy part of the vessel against which it presses. Conversely, a stent that is too small is unable to securely hold the graft in place. Thus, in order for the system proposed by Kreamer to function properly, the stents must be provided in a wide variety of sizes, and the proper size must be selected for each different application. Again, this increases the costs and complexity involved in the overall procedure and adds to the risk of improper graft placement.

SUMMARY OF THE INVENTION

The present invention is directed to a novel construction which allows a vascular graft to be applied easily and accurately without involving invasive surgery. The invention is particularly characterized by unique stents which hold the graft in place and which are constructed to naturally expand in a manner to assure that the ends of the graft are securely and properly pressed against healthy parts of the vascular wall on opposite sides of the diseased area.

In accordance with the invention, stents which are formed by flexible sheets are wound tightly around a spool. A synthetic graft is applied around the spool and fits closely around the stents in a collapsed state. A tubular sheath is closely sleeved around the graft to confine it and the stents while the spool is being inserted through the vessel and advanced to the area of the vascular damage.

When the spool has been properly positioned in the vessel, the sheath can be retracted to release the stents from their contracted conditions. The stents then unwind on the spool naturally under the influence of their inherent spring force. As the stents expand, they cause the graft to expand and press the ends of the graft against the vessel wall on opposite sides of the diseased part of the vessel. The graft is thus implanted securely in a position to span and essentially replace the diseased portion of the vessel.

The graft can have a tubular shape when implanted in a straight vessel. Alternatively, the graft can have a Y-shaped configuration when it is to be applied to a part of a vessel which branches. In this situation, the sheath may be eliminated and the stents can be held in the contracted condition by slip knots which are released when control cords are pulled. The Y-shaped graft also has a spring which is held compressed so that the branches of the graft lie against one another during insertion of the spool. A control cord can be pulled to release a slip knot for the spring, and the spring then expands to spread the branches of the graft apart so that they can fit in the vascular branches before the stents are allowed to expand.

DESCRIPTION OF THE DRAWINGS

In the accompanying drawings which form a part of the specification and are to be read in conjunction therewith and in which like reference numerals are used to indicate like parts in the various views:

FIG. 1 is a fragmentary perspective view of a vascular graft arrangement constructed according to a preferred embodiment of the present invention, with portions broken away for purposes of illustration and with the stents and graft contracted and the sheath shown in its withdrawn position;

FIG. 2 is a fragmentary sectional view showing the graft inserted into the vessel to the damaged vascular area, with the sheath sleeved around the graft and the graft and stents held by the sheath in the contracted conditions;

FIG. 3 is a fragmentary sectional view on an enlarged scale taken generally along line 3—3 of FIG. 2 in the direction of the arrows;

FIG. 4 is a fragmentary sectional view similar to FIG. 2, but showing the sheath withdrawn to allow the stents to expand and thereby expand the graft against the vessel walls in a position to span the damaged part of the vessel;

FIG. 5 is a sectional view on an enlarged scale taken generally along line 5—5 of FIG. 4 in the direction of the arrows;

FIG. 6 is a fragmentary sectional view depicting a branch portion of a vessel in which a graft arrangement constructed according to an alternative embodiment of the invention is being applied in its contracted state; and FIG. 7 is a fragmentary sectional view similar to FIG. 6, but showing the stents released and moving to their expanded conditions to press the graft against the vessel walls.

DETAILED DESCRIPTION OF THE INVENTION

Referring now to the drawings in more detail and initially to FIGS. 1-5, the present invention is directed to the repair of an artery or vessel such as the vessel 10 having a damaged wall portion 12. It should be noted that the invention is useful in the repair of vessel or artery walls which have been damaged by disease such as an aneurysm or by medical treatment such as aortic dissection, laser treatment, balloon angioplasty, or atherectomy.

The core of the device is formed by a tubular spool 14. The tubular spool 14 has an outer diameter considerably less than the inner diameter of the vessel 10 and is provided with an axial passage 16 which allows the spool 14 to be guided along a guide wire 18 which is threaded into the vessel to the area of the damaged wall 12. A pair of stents 20 are carried on the spool 14. One of the stents 20 is located near the leading end of the spool 14, and the other stent 20 is spaced away from the leading stent. One end of the trailing stent abuts a flange 22 which extends radially from the spool 14. The distance between the stents 20 depends upon the length of the graft that is being implanted, as will be explained in more detail.

Each of the stents 20 takes the form of a thin sheet which is initially flat but which is wound tightly around the spool 14 in a roll 24. Preferably, the material of which the stents are constructed is a thin metal foil which may be stainless steel. The sheets of which the stents are constructed are tightly wound on the spool 14 in a contracted condition. Because the stents are wound in a contracted condition, they naturally tend to expand under the influence of the inherent spring force they exert opposing their contraction. Thus, the rolls 24 are continuously urged from the contracted condition toward an expanded condition in which their diameter is greatly enlarged. When fully expanded, the outside diameter of each roll 24 is at least as great as the inside diameter of the vessel 10.

A tubular graft 26 is fitted closely around both of the stents 20 in a collapsed condition in which the graft 26 presents pleats or folds 28 (see FIG. 3 in particular). The graft 26 can be expanded from its collapsed condition such that the folds 28 are unfolded. When the graft 26 is fully expanded, its diameter is substantially equal to the inside diameter of the vessel 10. The graft 26 may be constructed of a suitable synthetic material. Alternatively, the graft 26 can be a section of a blood vessel that has been removed from some other part of the body.

The outside layer of each stent 20 has on one end a projecting tab 30 which is suitably secured to the inside surface of the graft 26. The connection between the tabs 30 and the graft 26 may be made by a rivet 32 or another suitable fastener.

A tubular sheath 34 is closely sleeved around the collapsed graft 26 and also around the flange 22 which is substantially equal in diameter to the diameter of the graft in its collapsed state. Since the graft 26 is closely confined within the sheath 34 and the stents 24 are closely confined within the graft 26, the sheath 34 serves to retain the rolls 24 in their contracted conditions and prevent them from expanding. Preferably, the sheath 34 has a cylindrical configuration and presents an outside diameter that is somewhat smaller than the inside diameter of the vessel 10.

In use, the spool 14, stents 20, graft 26 and sheath 34 are inserted as a unit into the vessel 10. The spool is advanced along the guide wire 18 until it has reached the area of the damaged wall 12. When the spool has been advanced to a position where the stents are located on opposite sides of the damaged wall 12, advancement of the spool is stopped. Then, the sheath 34 is retracted until it has been completely withdrawn from a position confining the graft 26. This releases the graft and also releases the stents 20 which then are able to assume their expanded conditions under the influence of the internal spring force which tends to unwind them on the spool 14. Consequently, the stents expand and likewise expand the graft until its opposite end portions have been pressed against the vessel wall in the position shown in FIGS. 4 and 5. The stents 20 exert forces against the graft which hold it securely against the healthy parts of the vessel wall located on opposite sides of the damaged area 12. It is noted that when the stents are expanded, there are still several overlapping layers of the stent which create friction that tends to press the stent outwardly against the graft. The graft is in turn frictionally held against the inside surface of the vessel wall.

Once the stents have expanded, the sheath 34 can be withdrawn from the vessel and the spool 14 and guide wire 18 can likewise be withdrawn. In this manner, the graft 26 is implanted to essentially replace the damaged wall 12 of the diseased vessel 10. It is noteworthy that the stents 20 naturally expand when the sheath 34 is withdrawn and that there is no need for the stents to be positively expanded or otherwise manipulated in order to properly hold the graft in place. All that is necessary is to advance the graft to the proper position and then retract the sheath 34.

In some cases, the spool can be initially advanced until its leading end is just short of the damaged wall. The advancement of the spool can thereafter be resumed while the sheath is held stationary. When the trailing stent clears the sheath, it is located on one side of the damaged area and both stents are expanded to secure the graft in place in the manner described previously.

FIGS. 6 and 7 depict an alternative embodiment of the invention which in many respects is similar to that previously described. The principal differences are in the shape of the graft and spool.

The embodiment of the invention shown in FIGS. 6 and 7 is intended to be implanted in a damaged vessel at a location where a pair of vascular branches 10a and 10b branch away from a main trunk 10c of the vessel. The damaged vessel wall 12 is adjacent to the junction between the branches 10a and 10b and the trunk 10c. The spool 114 which is included in the embodiment shown in FIGS. 6 and 7 includes a main portion 114a and a secondary branch 114b which has a flexible connection with the main portion 114a. In the initial position, the branch 114b is flexed such that it generally lies parallel to and along the main portion 114a.

The main portion 114a of the spool carries near its opposite ends two of the stents 20 which are spaced apart from one another, while the branch 114b carries on its free end a third stent 20. All three of the stents are tightly wound on the spool in the manner previously described.

In the embodiment shown in FIGS. 6 and 7, a Y-shaped graft 126 is fitted around the spool 114 and closely on the stents 20. The graft 126 has branches 126a and 126b for application to the respective branches 10a and 10b of the vessel. The graft 126 also has a main trunk portion 126c for application to the trunk 10c of the vessel. The graft is initially in a collapsed state, but when the graft 126 is applied to the vessel, it assumes the same Y-shaped configuration as the vessel.

The embodiment shown in FIGS. 6 and 7 does not make use of a sheath but instead holds the stents 20 in their contracted conditions with control cords. One of the cords 36 has a slip knot connection 38 with a flange 40 extending from the spool portion 114b at a position to be abutted by the corresponding stent 20. Another control cord 42 has a slip knot connection 44 with another flange 46 located on spool portion 114a at a location to be abutted by the stent 20 for the graft branch portion 126b. A third control cord 48 has a slip knot connection 50 with another flange 52. The flange 52 extends radially from the spool 114 near its leading end at a position to be abutted by one end of the stent 20 for the graft portion 126c.

The slip knots 38, 44 and 50 hold the stents 20 in their contracted conditions. In addition, a spring 54 is held in a compressed state by a slip knot 56 of another control cord 58. The spring 54 is located at the junction between the two branches 126a and 126b of the graft. In the normal state of the spring 54, its two legs are flexed apart and spread the graft portions 126a and 126b apart at the angle shown in FIG. 7. However, the spring 54 is held in the compressed state shown in FIG. 6 by the control cord 58 and its slip knot 56 while the graft is being inserted into the vessel.

The embodiment depicted in FIGS. 6 and 7 is applied in essentially the same manner as the embodiment shown in FIGS. 1–5. The stents are held in the contracted conditions by the slip knots, and the graft 126 is fitted around the stents in a collapsed state. The two branch portions 126a and 126b of the graft lie generally along one another because the spring 54 is held in the compressed state by the control cord 58 and its slip knot 56.

The spool 114 and all of the components carried on it are inserted into the vessel and advanced to the area of the damaged wall 12. When the position shown in FIG. 6 is reached, the control cord 58 is pulled to release the slip knot 56, thus allowing the spring 54 to expand such that branch portion 126c is able to enter the vessel branch 10a. At this point, the trunk portion 126a of the graft is located in the trunk portion 10c of the vessel and the branch portion 126b of the graft is located in the branch 10b of the vessel. Once the spring 54 has expanded, the spool 114 can be pulled back a short distance to cause graft portion 126a to enter the vessel branch 10a.

Once the graft has been properly positioned, the control cords 36, 42 and 48 can be pulled to release the slip knots 38, 44 and 50. All three of the stents 20 are thus released and expand under the influence of their internal spring force. The stents in turn expand the graft 126 and press it against the vessel walls. When the stents have fully expanded in the position shown in FIG. 7, the stent 20 in the branch portion 126a of the graft presses portion 126a securely against the wall of the vessel branch 10a. The stent in graft portion 126b likewise expands to secure the graft branch 126b against the wall of the vessel branch 10b. The third stent 20 expands to expand the trunk portion 126c of the graft against the wall of the trunk 10c.

In this manner, the Y-shaped graft is implanted in the area of the diseased vessel to span and essentially replace the damaged wall 12. The spool 114 and guide wire 18 can be withdrawn from the vessel once the graft has been properly positioned. It is noted that the graft 126 allows fluid flow through the vessel in the proper manner and direction without blocking or otherwise impeding the flow.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, we claim:

1. Apparatus for treating a damaged portion of a vessel, comprising:
   an elongated core;
   a pair of stents on said core at spaced apart locations, each stent comprising a thin flexible sheet tightly wound around the core in a roll having a contracted condition and urged to unwind to an expanded condition,
   each of said stent rolls being spirally wound on said core and having a tendency to radially expand, each said roll presenting a plurality of adjacent, arcuate layers of said sheet in a direction transverse to the longitudinal axis of said core;
   a flexible graft extending around both stents in a collapsed state and being expansible against the vessel to span the damaged portion thereof, each of said sheets including a tab secured to said graft; and
   means for maintaining said rolls in the contracted condition thereof to permit the core to be inserted into the vessel, said maintaining means being selectively releasable to allow said rolls to assume the expanded condition thereof to effect expansion of said graft against the vessel wall,
   said rolls in the expanded condition thereof each having at least an inner and an outer layer which overlap and bear against one another over a substantial portion of the circumstance of the inner layer, said expanded rolls securing said graft in said vessel.

2. Apparatus as set forth in claim 1, wherein said maintaining means comprises a sheath sleeved around said graft and movable axially relative to said core to release said stents and allow said rolls to assume the expanded condition.

3. Apparatus for treating a damaged portion of a vessel, comprising:
   an elongated core including an elongated stool having an axial passage therethrough for receiving a guide wire to facilitate insertion of the spool into the vessel;
   a pair of stents on said core at spaced apart locations, each stent comprising a thin flexible sheet tightly wound around the core in a roll having a contracted condition and urged to unwind to an expanded condition, each of said stent rolls being spirally wound on said core and having a tendency to radially expand, each said roll presenting a plurality of adjacent, arcuate layers of said sheet in a direction transverse to the longitudinal axis of said core;

a flexible graft extending around both stents in a collapsed state and being expansible against the vessel to span the damaged portion thereof; and means for maintaining said rolls in the contracted condition thereof to permit the core to be inserted into the vessel, said maintaining means being selectively releasable to allow said rolls to assume the expanded condition thereof to effect expansion of said graft against the vessel wall, said maintaining means comprising a sheath sleeved around said graft and movable axially relative to said core to release said stents and allow said rolls to assume the expanded condition, said rolls in the extended condition thereof each having at least an inner and an outer layer which overlap and bear against one another over a substantial portion of the circumference of the inner layer, said expanded rolls securing said graft in said vessel.

4. Apparatus for treating a damaged portion of a vessel, comprising:

an elongated core;

a pair of stents on said core at spaced apart locations, each stent comprising a thin flexible sheet tightly wound around the core in a roll having a contracted condition and urged to unwind to an expanded condition, each of said stent rolls being spirally wound on said core and having a tendency to radially expand, each said roll presenting a plurality of adjacent, arcuate layers of said sheet in a direction transverse to the longitudinal axis of said core;

a flexible graft extending around both stents in collapsed state and being expansible against the vessel to span the damaged portion thereof; and means for maintaining said rolls in the contracted condition thereof to permit the core to be inserted into the vessel, said maintaining means being selectively releasable to allow said rolls to assume the expanded condition thereof to effect expansion of said graft against the vessel wall, said maintaining means comprising a sheath sleeved around said graft and movable axially relative to said core to release said stents and allow said rolls to assume the expanded condition, said rolls in the expanded condition thereof each having at least an inner and an outer layer which overlap and bear against one another over a substantial portion of the circumference of the inner layer, said expanded rolls securing said graft in said vessel.

5. Apparatus for treating a damaged portion of a vessel at a location thereon where a main trunk of the vessel adjoins first and second branches thereof which cooperate with the main trunk to provide a Y configuration, said apparatus comprising:

a core;

a Y-shaped graft having a trunk portion and first and second branch portions extending from the trunk portion, said graft fitting on said core in a collapsed state and being expansible from the collapsed state to engage said trunk portion against the trunk of the vessel and said first and second branch portions against the respective first and second branches of the vessel;

a first stent on said core within said first branch portion of the graft;

a second stent on said core within said second branch portion of the graft;

a third stent on said core within said trunk portion of the graft, each of said stents comprising a thin flexible sheet arranged in a roll wound around the core in a contracted condition and each of said stents being urged to unwind from the collapsed condition to an expanded condition for pressing the graft against the vessel wall;

spring means for urging first and second branch portions of the graft to spread apart;

means for retaining said first and second branch portions together to allow said core to be inserted into the vessel to the damaged portion thereof, said retaining means being releasable to allow said first and second branch portions to spread apart under the influence of said spring means for entry of said branch portions into the respective first and second branches of the vessel; and means for maintaining each stent in the contracted condition while the core is being inserted into the vessel, said maintaining means being selectively releasable to permit the stents to assume the expanded condition for holding the first and second branch portions of the graft against the respective first and second branches of the vessel and for holding the trunk portion of the graft against the trunk of the vessel.

6. Apparatus as set forth in claim 5, including a flange on said spool for each stent, said rolls engaging the respective flanges at one end.

7. Apparatus as set forth in claim 6, wherein said maintaining means comprises a control cord for each stent having a slip knot connection with the corresponding flange for holding the corresponding roll in the contracted condition, each slip knot connection releasing the corresponding roll when the control cord is pulled.

8. A method of treating a damaged vessel wall, comprising the steps of:

winding a plurality of flexible metal sheets into rolls carried on a core with each roll being urged to unwind from a contracted condition to an expanded condition;

applying a graft over said rolls with the graft in a collapsed state but being expansible to span the damaged wall with the graft engaging the vessel wall;

inserting said core into the vessel to the damaged wall with the rolls in the contracted condition and the graft in the collapsed state; and releasing said rolls to allow them to assume the expanded condition and thereby expand the graft and hold it against the vessel wall at a location to span the damaged vessel wall.

9. A method as set forth in claim 8, including the step of sleeving a sheath closely around the graft to hold the rolls in the contracted condition and maintain the graft in the collapsed state while the core is being inserted in the vessel, said releasing step comprising effecting relative axial movement between the sheath and core to displace the sheath from a position confining the rolls and graft.

10. A method as set forth in claim 8, wherein:

the vessel includes a main trunk and a pair of branches extending from the trunk; and said graft includes a trunk portion for application to the trunk of the vessel and a pair of branch portions for application to the respective branches of the vessel.

11. A method as set forth in claim 10, including the steps of:
- holding said branch portions of the graft together while the core is being inserted in the vessel; and
- effecting spreading of said branch portions apart to allow them to enter the respective branches of the vessel prior to said releasing step.

* * * * *